United States Patent
Munoz

(10) Patent No.: US 7,070,984 B2
(45) Date of Patent: Jul. 4, 2006

(54) BIOLOGICAL CONTROL OF SOIL-BORN FUNGAL PATHOGENS

(75) Inventor: Antonio Munoz, 6300 W. Little York, #112, Houston, TX (US) 77091

(73) Assignees: Antonio Munoz, Houston, TX (US); Rafael Munoz, Houston, TX (US); Jose Munoz, Houston, TX (US); Clotilde Munoz, Houston, TX (US)

( * ) Notice: Subject to any disclaimer, the term of this patent is extended or adjusted under 35 U.S.C. 154(b) by 406 days.

(21) Appl. No.: 10/236,078

(22) Filed: Sep. 4, 2002

(65) Prior Publication Data

US 2003/0092574 A1    May 15, 2003

Related U.S. Application Data

(63) Continuation of application No. 09/492,491, filed on Jan. 27, 2000, now abandoned.

(60) Provisional application No. 60/131,285, filed on Apr. 27, 1999, provisional application No. 60/117,912, filed on Jan. 29, 1999.

(51) Int. Cl.
 *C12N 1/14* (2006.01)

(52) U.S. Cl. .................. 435/254.6; 424/93.5; 504/117
(58) Field of Classification Search ..................... None
See application file for complete search history.

(56) References Cited

U.S. PATENT DOCUMENTS

| | | | |
|---|---|---|---|
| 3,674,649 A | | 7/1972 | Formisano et al. |
| 4,127,964 A | | 12/1978 | Mee |
| 4,489,161 A | * | 12/1984 | Papavizas ................ 435/256.7 |
| 4,668,512 A | * | 5/1987 | Lewis et al. ................ 424/93.5 |
| 4,752,316 A | | 6/1988 | Plovanich et al. |
| 5,192,686 A | * | 3/1993 | Ahmad et al. ........... 424/256.1 |
| 5,393,317 A | | 2/1995 | Robinson |

FOREIGN PATENT DOCUMENTS

FR    2141588 A    6/1971

* cited by examiner

*Primary Examiner*—Irene Marx
(74) *Attorney, Agent, or Firm*—Knobbe, Martens, Olson & Bear LLP

(57) ABSTRACT

This invention relates generally to biological control of plant disease. The invention discloses an antagonistic *Trichoderma* fungal strain that targets soil-born fungi from the genus *Fusaria* and the genus *Rhizoctonia*.

8 Claims, No Drawings

BIOLOGICAL CONTROL OF SOIL-BORN FUNGAL PATHOGENS

The present application claims priority under 35 U.S.C.§119(e) to U.S. Provisional Application 60/117,912, filed on Jan. 29, 1999 and U.S. Provisional Application 60/131,285, filed on Apr. 27, 1999, the disclosures of which are incorporated herein by reference. The present application also claims priority under 35 U.S.C. §120 as a continuation of U.S. patent application Ser. No. 09/492,491, filed Jan. 27, 2000 now abandoned.

BACKGROUND OF THE INVENTION

1. Field of the Invention

This invention relates generally to biological control of plant disease. The invention discloses an antagonistic *Trichoderma viride* fungal strain that targets soil-born fungi from the genus *Fusaria* and the genus *Rhizoctonia*.

2. Description of the Related Art

Soil-borne fungal pathogens from the genus *Fusaria* and the genus *Rhizoctonia* are extremely harmful to turf grasses and crops. These pathogens attack the roots of plants and cause rotting. In crops they cause seedling blight and damping-off disease. Turf grasses are especially susceptible to these soil-born fungal pathogens. Clipping and trampling on turf grass places stress on the grass, increasing susceptibility to fungal infection. New growth also increases the susceptibility of these plants to fungal infection.

Current soil treatments use pesticides to target these fungal pathogens. Unfortunately, these pesticides are often toxic to animals and humans. Moreover, if they move through run off waters into other areas they can do environmental damage by contaminating water and soil.

An alternative approach to the treatment of fungal infection is biological control. In this type of treatment, an antagonistic organism is used to interfere with the processes of a fungal pathogen. For example, it has been demonstrated that the fungus *Myrothecium roridum* works antagonistically against the *Phytophthora* organism to prevent diseases in plant crops.

A need exists for a soil treatment that attacks the *Fusaria* and *Rhizoctonia* pathogens in a way that is non-toxic to humans and animals.

SUMMARY OF THE INVENTION

The current invention discloses a novel strain of *Trichoderma viride*. It also discloses a composition of matter comprising a mixture of this novel strain of *Trichoderma viride* and organic matter. The organic matter may be selected from the group comprising cereal grains, peat and compost. The current invention also relates to a method of treating plant disease caused by the *Fusaria* or *Rhizoctonia* fungal pathogens, comprising applying the novel strain of *Trichoderma viride* to the soil in which the diseased plants are growing.

DETAILED DESCRIPTION OF THE PREFERRED EMBODIMENT

The current invention discloses a novel strain of *Trichoderma viride*, named Li 49. This strain is used as part of a treatment to control plant diseases caused by the *Fusaria* and *Rhizoctonia* fungal pathogens. The treatment works through three different mechanisms of biological control. The first mechanism is competition, where the *Trichoderma* strain Li 49 eliminates the soil-borne pathogens by rapidly colonizing the space that the pathogens inhabit. The second mechanism is parasitism, in which the *Trichoderma* strain Li 49 penetrates the hyphae of the host and destroys the pathogens. The third mechanism is antibiosis, where the *Trichoderma* strain produces compounds that are toxic to the pathogens. The *Trichoderma* strain was deposited with the ATCC, 10801 University Boulevard, Manassas, Va., on Jan. 26, 2000 and assigned Patent Designation PTA-1225.

In addition to controlling the plant disease, the treatment helps to restore microbial flora in the soil.

*Trichoderma viride* isolates were obtained from 98 different rhyzosphere soil samples from several different ecosystems and agrosystems in Mexico. The soil samples were cleaned, screened, and plated in a variety of growth media for soil fungi. After plating and incubation, Trichoderma colonies were isolated and observed under the microscope. The isolates that demonstrated the most vigorous Trichoderma growth were selected and transferred to new culture media. The *Trichoderma* fungus was purified and grown in an axenic culture. Further investigation revealed a new strain of *Trichoderma viride* identified as Li 49. This *Trichoderma* strain came from forest trees in the Sierra Madre Occidental in the state of Nayarit, Mexico.

The *Trichoderma viride* strain Li 49 may be applied to soil by itself or in a mixture. The mixture may consist of strain Li 49 and any appropriate vehicle known in the art. Preferably the strain Li 49 is applied in the soil treatment mixture of the present invention.

The soil treatment mixture of the present invention was prepared by combining the Trichoderma isolate with organic matter. The fungus may make up from 1 to 90% of the soil treatment mixture by weight. In the preferred embodiment, the fungus makes up at least 10% of the soil treatment mixture by weight. The organic matter may be any known in the art. However, in the preferred embodiment, the organic matter in the soil treatment mixture comprises cereal grains, peat and compost. The organic matter is ground, homogenized and added to the fungal isolate to produce the soil treatment mixture of the present invention. Because the fungal isolate is grown in culture, the soil treatment mixture will contain some trace of culture media.

The soil treatment mixture may be applied to the soil by itself. However it may also be applied to the soil in combination with organic compost and/or a soil softening mixture. The soil treatment mixture is preferably dispersed in water and applied by spraying. For each acre of crop to be treated, from 5 to 50 pounds of the soil treatment mixture may be applied. In the preferred embodiment, 5 pounds of the soil treatment mixture is dispersed in 20 gallons of water and applied to each acre of crop to be treated. This treatment can be re-applied from 1 to 6 times each year. In the preferred embodiment, the soil treatment mixture is applied every 3 months.

EXAMPLE 1

When applied to sod, results are noticeable in 3 to 4 weeks after application and last for a period of 6 to 8 weeks. During spring months, results may be seen in 2 to 3 weeks. Diseased areas, identified as yellow or brown patches, are observed to shrink, and the sod takes on a uniform healthy green look.

EXAMPLE 2

A sample of the soil treatment mixture of the present invention was subject to chemical analysis.

| PERCENTAGE (DRY WEIGHT) | % | lb/ton |
|---|---|---|
| Total Nitrogen (N) | 2.02 | 40.40 |
| Soluble Nitrate ($NO_3$) | 0.30 | 6.08 |
| Total Phosphorus (P) | 0.44 | 20.16 $P_2O_5$ |
| Soluble Phosphate ($PO_4$) | 0.09 | 1.76 |
| Potassium (K) | 0.40 | 9.64 $K_2O$ |
| Sodium (Na) | 0.02 | 0.40 |
| Calcium (Ca) | 0.06 | 1.60 |
| Magnesium (Mg) | 0.12 | 2.40 |
| Zinc (Zn) | 0.0049 | 0.10 |
| Iron (Fe) | 0.0060 | 0.19 |
| Manganese (Mn) | 0.0056 | 0.11 |
| Copper (Cu) | 0.0009 | 0.02 |
| Boron (B) | 0.0010 | 0.02 |

What is claimed is:

1. An isolated culture of a strain of *Trichoderma viride* on deposit with the ATCC and identified by Patent Deposit Designation PTA-1225.

2. A composition of matter comprising a mixture of the stain of *Trichoderma viride* of claim 1 and organic matter.

3. The composition of matter of claim 2 wherein the organic matter is selected from the group consisting of cereal grains, peat and compost.

4. A method of treating plant disease caused by the *Fusarium* or *Rhizoctonia* fungal pathogens, comprising:
 applying the strain of *Trichoderma viride* of claim 1 to the soil in which the diseased plants are growing.

5. The method of claim 4 wherein the strain of *Trichoderma viride* of claim 1 is applied as part of a mixture.

6. The method of claim 5 wherein the mixture is the composition of matter of claim 2.

7. The method of claim 6 wherein the mixture comprises 10% *Trichoderma viride* by weight.

8. The method of claim 7 wherein the mixture is applied at a dose of 5 pounds per acre.

* * * * *

UNITED STATES PATENT AND TRADEMARK OFFICE
CERTIFICATE OF CORRECTION

PATENT NO. : 7,070,984 B2
APPLICATION NO. : 10/236078
DATED : July 4, 2006
INVENTOR(S) : Antonio Munoz It is certified that error appears in the above-identified patent and that said Letters Patent is hereby corrected as shown below:

In Col. 1, line 11, After "2000" insert -- , --.

In Col. 1, line 22, Delete "*Rhizoctonia*are" and insert -- *Rhizoctonia* are --, therefore.

In Col. 1, line 43, Delete "*Rhizoctonia*pathogens" and insert -- *Rhizoctonia* pathogens --, therefore.

In Col. 4, line 2, In Claim 2, delete "stain" and insert -- strain --, therefore.

Signed and Sealed this

Twentieth Day of October, 2009

David J. Kappos
*Director of the United States Patent and Trademark Office*